United States Patent [19]

Sellstedt et al.

[11] 4,316,037
[45] Feb. 16, 1982

[54] N-BENZYL AND N-SUBSTITUTED BENZYL TETRAZOLE-5-CARBOXYLIC ACIDS AND THE PREPARATION THEREOF

[75] Inventors: John H. Sellstedt, Pottstown; Dieter H. Klaubert, West Chester, both of Pa.

[73] Assignee: American Home Products Corporation, New York, N.Y.

[21] Appl. No.: 761,149

[22] Filed: Jan. 21, 1977

[51] Int. Cl.³ .............................................. C07D 257/02
[52] U.S. Cl. .................................................... 548/253
[58] Field of Search ..................... 260/308 D; 548/253

[56] References Cited

U.S. PATENT DOCUMENTS 3,516,997  6/1970  Takano et al. ........................ 544/27
3,743,646  7/1973  Buckler ............................. 260/308 D
3,962,272  6/1976  Katner .............................. 260/308 D

FOREIGN PATENT DOCUMENTS 1364919  8/1974  United Kingdom ........... 260/308 D

Primary Examiner—Donald G. Daus
Assistant Examiner—D. B. Springer
Attorney, Agent, or Firm—Richard K. Jackson

[57] ABSTRACT

N-Protected-tetrazole-5-carboxylic acid derivatives of the formula:

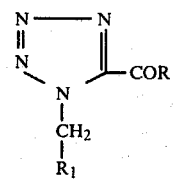

in which
R is —OM, halo or lower alkoxy wherein M is hydrogen, an alkali metal or an alkaline earth metal; and
$R_1$ is phenyl, 4-methoxyphenyl, 2,4-dimethoxyphenyl or 2,4,6-trimethoxyphenyl, are produced by addition of $R_1$—$CH_2$—$N_3$ to a lower alkyl cyanoformate followed by saponification, optional acidification, and conversion to the carbonyl halide. The N-protected tetrazole-5-carbonylhalides are intermediates for the production of anti-allergic agents.

12 Claims, No Drawings

N-BENZYL AND N-SUBSTITUTED BENZYL TETRAZOLE-5-CARBOXYLIC ACIDS AND THE PREPARATION THEREOF

BACKGROUND OF THE INVENTION

The production of 1,5-substituted tetrazoles by addition of an organic azide to a nitrile was extended from intramolecular cyclizations to intermolecular additions by Carpenter, J. Org. Chem. 27, 2085(1962) with the discovery that activation of the nitrile by electron-withdrawing groups (per haloalkylnitriles) afforded facile reactions without a catalyst. It was previously known that attempts to saponify 5-carboethoxytetrazole led directly to the unsubstituted 1H-tetrazole, presumably because the 1H-tetrazole-5-carboxylic acid was unstable, spontaneously decarboxylating to the unsubstituted product, Oliveri-Mandalia, Gass. Chem. Ital. 41, 59 (1911). Recently, Katner disclosed in U.S. 3,962,272 a new procedure for producing 5-acyl-1H-tetrazole-1-acetate esters by reaction of an acyl cyanide with azidoacetic acid or ester at elevated temperatures.

DESCRIPTION OF THE INVENTION

In accordance with this invention there is provided a process for the production of 1,5-disubstituted-1H-tetrazoles of the formula:

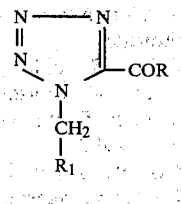

in which
R is —OM, halo or lower alkoxy wherein M is hydrogen, an alkali metal or an alkaline earth metal; and
$R_1$ is phenyl, 4-methoxyphenyl, 2,4-dimethoxyphenyl or 2,4,6-trimethoxyphenyl, which comprises adding an azide of the formula $R_1$—$CH_2$—$N_3$ to a lower alkyl cyanoformate at a temperature between about 85° C. to about 250° C. in a closed vessel under autogenous pressure for a time sufficient to effect the addition reaction. The resulting N-protected tetrazole-5-carboxylic acid lower alkyl ester is treated with an alkali metal or alkaline earth metal hydroxide to produce the corresponding salt, which is readily converted to the free carboxylic acid by treatment with an equivalent amount of a strong acid or directly converted to the corresponding 5-carbonyl halide by treatment with a halogenating agent, preferably oxalyl chloride or bromide. The free 5-carboxylic acid or salt may also be converted to the acid halide by treatment with conventional agents employed in the production of acid halides such as $PCl_5$, $PCl_3$, $POCl_3$, $SOCl_2$, and the like in the presence of an acid acceptor such as pyridine.

The N-protected tetrazole-5-carbonyl halide products and the intermediates formed in their production, represent the compound aspect of this invention. The carbonyl halide products are intermediates useful in the production of antiallergic agents such as are disclosed in our co-pending application Ser. No. 669,570, filed March 23, 1976, now U.s. Pat. No. 4,013,647. In practice, the N-protected-tetrazole-5-carbonyl halides of this invention are condensed with a desired amine and the protective group of the tetrazole is removed to yield the desired anti-allergic agent. Thus, the N-protecting group present in the initial azide reactant is carried through the entire reaction sequence leading to the desired anti-allergic agent. Hence, the protecting group ($R_1$—$CH_2$—) must be stable under all reaction conditions involved in the multi-step process resulting in the production of a desired ultimate compound while having the attribute of facile removal, when desired, under conditions that will otherwise not affect that ultimate product. It has been discovered that the $R_1$—$CH_2$ protecting groups are ideally suited for the purpose stated in that the $R_1$ group defined supra, provides an inductive effect which serves as a carbonium ion stabilizer, protecting the tetrazole from rearrangement and/or decarboxylation and providing for easy ultimate removal by treatment with a strong acid or by hydrogenation.

The compound aspect of this invention embraces compounds of the formula:

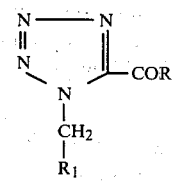

in which
R is —OM, halo or lower alkoxy, wherein M is hydrogen, an alkali metal cation or an alkaline earth metal cation; and
$R_1$ is phenyl, 4-methoxyphenyl, 2,4-dimethoxyphenyl or 2,4,6-tri-methoxyphenyl.

The term "halo" is intended to embrace the chloro and bromo groups. The expression "lower alkoxy" is intended to embrace methoxy, ethoxy, i-propoxy, n-propoxy, butoxy and pentoxy groups.

The following examples are presented to illustrate the process of preparation of representative compounds embraced by the disclosed invention.

EXAMPLE 1

1-Benzyl-5-carboethoxytetrazole

An equimolar mixture of benzyl azide and ethyl cyanoformate is heated in a bomb under antogenous pressure at 150° C. for 4 hours. The resulting yellow oil is crystallized from hexane to give the title compound, m.p. 58°–61° C.

Benzyl azide is prepared by the method of Fr. Moulin, Helv. Chim. Acta 35, 167 (1952).

EXAMPLE 2

Potassium 1-Benzyl-1H-tetrazole-5-carboxylate

To a solution of 1-benzyl-5-carboethoxy tetrazole prepared in Example 1, in warm absolute ethanol is added a stoichiometric excess of KOH in water to precipitate crystalline 1-benzyl-1H-tetrazole-5-carboxylic acid potassium salt.

EXAMPLE 3

1-Benzyl-1H-tetrazole-5-carbonyl chloride

The potassium salt produced in Example 2, and pyridine are stirred at 6° C. in benzene followed by rapid addition of oxalyl chloride. After stirring one half hour at 15° C. the mixture is stripped at 15° C., and scrubbed with two portions of benzene at 15° C. to yield 1-benzyl-1H-tetrazole-5-carbonyl chloride.

EXAMPLE 4

1-(p-Methoxybenzyl)-5-carboethoxytetrazole

A mixture of 16.3 g. of p-methoxybenzyl azide and 10.9 g. of ethyl cyanoformate is treated as above. The oil is dissolved in diethyl ether and cooled to −76° C. to give the product which is recrystallized from cyclohexane, (17 g., 10% yield, m.p. 54°–56° C.

Anal. Calc'd. for $C_{12}H_{14}N_4O_3$: C, 54.95; H, 5.38; N, 21.36. Found: C, 55.05; H, 5.41; N, 21.43.

p-Methoxybenzyl azide is prepared by stirring a mixture of 35 g. of p-methoxybenzyl chloride and 20 g. of sodium azide in 300 ml. dimethylformamide at room temperature for 30 minutes. The mixture is poured into water and extracted with benzene. The extracts are dried, evaporated to dryness and the residue is vacuum distilled, 34 g., bp 72°–75° C. (0.05 mm) (lit. 118°–118.5° C., 10 mm., reference in example 1).

p-Methoxybenzyl chloride is prepared by the method of C. G. Swain and W. P. Langsdorf, Jr., J. Am. Chem. Soc. 73, 2813 (1951).

EXAMPLE 5

Sodium 1-(p-Methoxybenzyl)-1H-tetrazole-5-carboxylate

Following the procedure of Example 2, 1-(p-methoxybenzyl)-5-carboethoxy tetrazole is dissolved in warm absolute ethanol. A slight stoichiometric excess of NaOH in water is added to precipitate the sodium salt.

EXAMPLE 6

1-(p-Methoxybenzyl)-1H-tetrazole-5-carbonyl chloride

Following the procedure of Example 3, the sodium salt produced in Example 5 is stirred with pyridine in benzene at 6° C. with rapid addition of oxalyl chloride. The mixture is stirred at 15° C. for one half hour, stripped and scrubbed twice with benzene to yield 1-(p-methoxybenzyl)-1H-tetrazole-5-carbonyl chloride.

What is claimed is:

1. A compound of the formula:

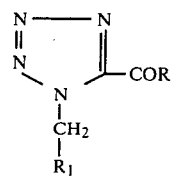

in which
R is —Om, halo or lower alkoxy wherein M is hydrogen, an alkali metal cation or an alkaline earth metal cation; and
$R_1$ is phenyl, 4-methoxyphenyl, 2,4-dimethoxyphenyl, or 2,4,6-trimethoxyphenyl.

2. The compounds of claim 1 in which R is a lower alkoxy radical selected from the group consisting of methoxy, ethoxy, propoxy, i-propoxy, butoxy and pentoxy.

3. The compounds of claim 1 in which R is chloro or bromo.

4. The compounds of claim 1 in which R is —OH.

5. The compounds of claim 1 in which R is —OM and M is sodium or potassium.

6. A compound of claim 2 which is 1-benzyl-5-carboethoxy tetrazole.

7. A compound of claim 2 which is 1-(p-methoxybenzyl)-5-carboethoxy tetrazole.

8. A compound of claim 3 which is 1-benzyl-1H-tetrazole-5-carbonyl chloride.

9. A compound of claim 3 which is 1-(p-methoxybenzyl)-1H-tetrazole-5-carbonyl chloride.

10. A compound of claim 5 which is potassium 1-benzyl-1H-tetrazole-5-carboxylate.

11. A compound of claim 5 which is sodium 1-(p-methoxybenzyl)-1H-tetrazole-5-carboxylate.

12. A process for the production of a lower alkyl ester of a 1H-tetrazole-5-carboxylic acid which comprises adding an azide of the formula $R_1$—$CH_2$—$N_3$ in which $R_1$ is selected from the group consisting of phenyl, 4-methoxyphenyl, 2,4-dimethoxyphenyl and 2,4,6-trimethoxyphenyl, to a lower alkyl cyanoformate at a temperature between about 85° C. to about 250° C. in a closed vessel under autogenous pressure for a time sufficient to effect the addition reaction.

* * * * *

UNITED STATES PATENT OFFICE
CERTIFICATE OF CORRECTION

Patent No. 4,316,037                    Dated February 16, 1982

Inventor(s) John H. Sellstedt and Dieter H. Klaubert

It is certified that error appears in the above-identified patent and that said Letters Patent are hereby corrected as shown below:

Column 2, line 11, "$R_1-CH_2 13$" should read -- $R_1-CH_2-$ -- ;

Claim 1, column 4, line 11, "-Om" should read ---OM -- ;

Delete claim 12.

On the title page, "12 Claims" should read -- 11 Claims --.

Signed and Sealed this

Twentieth Day of July 1982

[SEAL]

Attest:

GERALD J. MOSSINGHOFF

Attesting Officer            Commissioner of Patents and Trademarks